United States Patent [19]

Waring

[11] 4,176,194
[45] Nov. 27, 1979

[54] OXYALKANOIC ACID DERIVATIVES

[75] Inventor: Wilson S. Waring, Macclesfield, England

[73] Assignee: Imperial Chemical Industries Limited, London, England

[21] Appl. No.: 887,858

[22] Filed: Mar. 17, 1978

[30] Foreign Application Priority Data

Apr. 1, 1977 [GB] United Kingdom ............... 13837/77

[51] Int. Cl.$^2$ ..................... A61K 31/24; C07C 131/00
[52] U.S. Cl. .................................... 424/309; 424/316; 424/319; 424/324; 260/558 A; 260/448 R; 560/35; 562/440
[58] Field of Search ....................... 260/518 A, 448 R; 424/324, 309, 319; 560/35; 562/440

[56] References Cited

U.S. PATENT DOCUMENTS

| | | | |
|---|---|---|---|
| 3,853,955 | 12/1974 | Van Dijk et al. | 560/35 |
| 4,071,686 | 1/1978 | Van Dijk et al. | 560/35 |

FOREIGN PATENT DOCUMENTS 46-7932  2/1971  Japan ......................................... 560/35

OTHER PUBLICATIONS

Forrester et al, Chem. Soc., Chem. Commun., (8), pp. 291–292, (1975).

*Primary Examiner*—James O. Thomas, Jr.
*Assistant Examiner*—G. T. Breitenstein
*Attorney, Agent, or Firm*—Cushman, Darby & Cushman

[57] ABSTRACT

The invention concerns novel diarylmethyleneamino-oxyalkanoic acid derivatives which possess useful analgesic properties in warm-blooded animals. In addition certain of the derivatives also possess useful anti-inflammatory properties. Accordingly, the invention embraces oxyalkanoic acids, and simple esters and amides and non-toxic salts thereof, of the general formula:

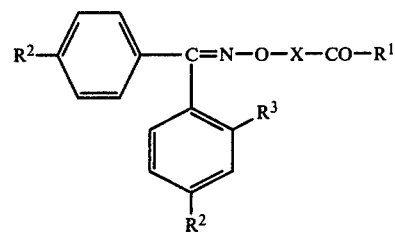

I together with pharmaceutical compositions thereof, for use in the treatment of painful inflammatory joint diseases. In addition, the invention provides as a further feature various analogy processes for the manufacture of compounds of formula I.

A representative compound of the invention is di-(4-chlorophenyl)methyleneamino-oxyacetic acid which has both analgesic and anti-inflammatory properties.

5 Claims, No Drawings

OXYALKANOIC ACID DERIVATIVES

This invention relates to oxyalkanoic acid derivatives and more particularly it relates to diarylmethyleneamino-oxyalkanoic acid derivatives which possess analgesic properties and, in some cases, in addition anti-inflammatory properties.

According to the invention there is provided a diarylmethyleneamino-oxyalkanoic acid derivative of the formula:

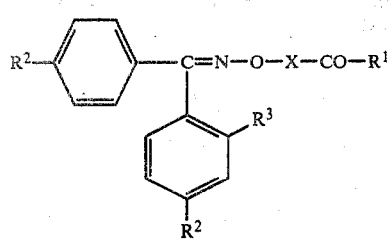

wherein $R^1$ is a hydroxy, amino or di-($C_{1-4}$-alkyl)amino radical, or a $C_{1-4}$-alkoxy radical optionally bearing a di-($C_{1-4}$-alkyl)amino radical; $R^2$ is a halogen atom, $C_{1-4}$-alkoxy, $C_{1-4}$-alkyl or hydroxy radical; $R^3$ is hydrogen or a halogen atom; and X is a methylene, trimethylene, ethylidene ($CH_3.CH<$), isopropylidene [$(CH_3)_2C<$] or propylidene ($CH_3CH_2.CH<$) diradical; or, for a compound of formula I wherein $R^1$ is a hydroxy radical, a pharmaceutically acceptable base-addition salt thereof; or for a compound of formula I wherein $R^1$ is a $C_{1-4}$-alkoxy radical bearing a di-($C_{1-4}$-alkyl)amino radical, a pharmaceutically acceptable acid-addition salt thereof.

A particular value for $R^1$ when it is a di-($C_{1-4}$-alkyl)amino radical is, for example, a dimethylamino or diethylamino radical; and when it is a $C_{1-4}$-alkoxy radical optionally bearing a di-($C_{1-4}$-alkyl)amino radical is, for example, a methoxy or ethoxy radical optionally bearing a dimethylamino or diethylamino radical.

A particular value for $R^2$ or $R^3$ when it is a halogen atom is, for example, a fluorine, bromine or chlorine atom, of which a chlorine atom is preferred.

A particular value for $R^2$ when it is a $C_{1-4}$-alkoxy radical is, for example, a methoxy or ethoxy radical; and when it is a $C_{1-4}$-alkyl radical is, for example, a methyl or ethyl radical.

It will be observed that within the above general definition of formula I there are comprised various particular and individual compounds of the invention, namely those compounds of formula I wherein one of $R^1$, $R^2$, $R^3$ and X, has one of the above defined particular values, and the remainder of $R^1$, $R^2$, $R^3$ and X have any of the above defined general or particular values; together, when $R^1$ is a hydroxy radical, with the pharmaceutically acceptable salts thereof. However specific groups of compounds of formula I which are of particular interest comprise those compounds of formula I wherein:

(a) $R^1$ is a hydroxy or a $C_{1-4}$-alkoxy radical;
(b) $R^1$ is a $C_{1-4}$-alkoxy radical bearing a di-($C_{1-4}$-alkyl)amino radical;
(c) $R^1$ is an amino or di-($C_{1-4}$-alkyl)amino radical;
(d) $R^3$ is hydrogen;
(e) $R^2$ is a halogen atom;
(f) X is a methylene radical; and
(g) $R^1$ has the meaning of group (a) and (b) taken together and in each group the remainder of $R^1$, $R^2$, $R^3$ and X have any of the above defined general or particular values; together with the pharmaceutically acceptable salts thereof.

A preferred group of compounds of formula I comprises those compounds wherein $R^1$ is a hydroxy, or $C_{1-4}$-alkoxy radicals, $R^2$ is a halogen atom, $R^3$ is hydrogen or a halogen atom, and X is a methylene radical; together, when $R^1$ is a hydroxy radical, with the pharmaceutically acceptable base-addition salts thereof.

Specific compounds of formula I are described in the accompanying Examples but, of those, compounds which are of particular interest are di-(4-chlorophenyl)-methyleneamino-oxyacetic acid and (4-chlorophenyl)(2,4-dichlorophenyl)methyleneamino-oxyacetic acid; together with the pharmaceutically acceptable base-addition salts thereof; and ethyl di-(4-chlorophenyl)methyleneamino-oxyacetate.

A particular base-addition salt of a compound of formula I wherein $R^1$ is a hydroxy radical is, for example, an alkali metal or alkaline earth metal salt, for example a sodium, potassium, calcium or magnesium salt, an aluminium salt, for example an aluminium hydroxide di-salt, or a salt with an organic base affording a pharmaceutically acceptable cation, for example triethanolamine or benzylamine.

A particular acid-addition salt of a compound of formula I wherein $R^1$ is an alkoxy radical bearing a dialkylamino radical, is, for example, a salt of an inorganic acid, for example hydrochloric or sulphuric acid, or of an organic acid affording a pharmaceutically acceptable anion, for example oxalic acid or maleic acid.

The novel compounds of formula I may be prepared by any process applicable to the manufacture of chemically analogous compounds. Such processes are provided as a further feature of the invention and are exemplified by the following in which $R^1$, $R^2$, $R^3$ and X have the meanings defined hereinabove unless stated otherwise:

(a) Reacting a salt of an oxime of the formula:

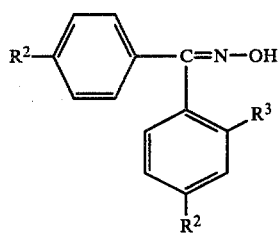

with a halogen derivative of the formula:

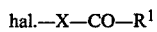

wherein hal. is a chlorine, bromine or iodine atom.

A particular salt of an oxime of formula II is, for example, an alkali metal salt, for example a sodium or potassium salt.

The required salt of the oxime of formula II is preferably performed by reaction of an oxime of formula II with a suitable base, for example an alkali metal hydride or alkoxide, for example sodium hydride or ethoxide, conveniently in a suitable solvent which may also function as solvent for the reaction with the halogenated derivative of formula III. A particularly suitable solvent when sodium hydride is used as the base is, for example, dimethylformamide, and when sodium ethoxide is used, is, for example, ethanol.

Alternatively, the required salt of the oxime of formula II may be formed during the reaction by reacting a free oxime of formula II with the halogenated derivative of formula III in the presence of a suitable base, for example triethylamine, and conveniently in a suitable solvent, for example dimethyl formamide.

The reaction is preferably carried out at a temperature of, for example, 20° to 100° C.

(b) Reacting a benzophenone of the formula:

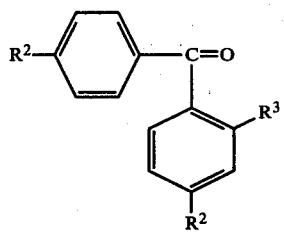

with a hydroxylamine derivative of the formula:

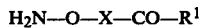        V

The reaction is conveniently carried out in a suitable solvent, for example pyridine, at a temperature of, for example, 50° to 100° C., and in which case the hydroxylamine derivative of formula V is conveniently used as a hydrogen halide salt, for example as its hydrochloride salt.

(c) For a compound of formula I wherein X is a trimethylene radical, reacting a salt of an oxime of formula II with γ-butyrolactone.

The reaction is preferably carried out in a suitable solvent, for example, N-methyl-2-pyrrolidone or toluene and conveniently at a temperature of, for example, 50° to 200° C.

A particularly suitable salt of an oxime of formula II is, for example, an alkali metal salt, for example, a sodium or potassium salt, which may conveniently be formed as described hereinabove for process (a).

An excess of the γ-butyrolactone is conveniently employed in the process.

(d) For a compound of formula I wherein $R^1$ is a hydroxy radical, hydrolysing an ester of the formula:

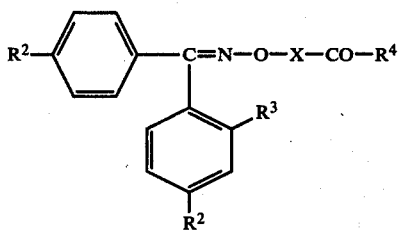

wherein $R^4$ is a $C_{1-6}$-alkoxy radical for example a methoxy or ethoxy radical, a benzyloxy or phenoxy radical.

The hydrolysis is conveniently carried out, for example, in the presence of base, for example sodium or potassium hydroxide, in a suitable solvent, for example ethanol or methanol, optionally mixed with water. Elevated temperatures, for example 50° to 100° C., may be employed to increase the rate of hydrolysis. The necessary ester starting materials may be obtained by an analogous procedure to that in process (a) or (b) hereinabove.

Whereafter, when a compound of formula I wherein $R^1$ is a $C_{1-4}$-alkoxy radical optionally bearing a di-($C_{1-4}$-alkyl)amino radical is required, a compound of formula I wherein $R^1$ is a hydroxy radical is esterified by a conventional procedure.

A suitable esterification procedure involves, for example, reacting an alkali metal salt, for example a sodium or potassium salt, of a compound of formula I wherein $R^1$ is a hydroxy radical with a compound of the formula $R^5$.hal wherein $R^5$ is a $C_{1-4}$-alkyl radical optionally bearing a di-($C_{1-4}$-alkyl)amino radical and hal. is a chlorine, bromine or iodine atom, preferably in a solvent, such as dimethylformamide and at a temperature in the range, for example, 15°-30° C.

Whereafter, when a base-addition salt is required, a compound of formula I wherein $R^1$ is a hydroxy radical is reacted with a suitable base affording a pharmaceutically acceptable cation, and when an acid-addition salt is required, a compound of formula I wherein $R^1$ is a $C_{1-4}$-alkoxy radical bearing a di-($C_{1-4}$-alkyl)amino radical is reacted with a suitable acid-affording a pharmaceutically acceptable anion, in each case using conventional procedures.

The necessary starting materials required for the above processes may be made according to well known procedures of organic chemistry.

The analgesic properties of compounds of formula I may be demonstrated using a standard test procedure involving the measurement of the inhibition of writhing in mice induced by intraperitoneal injection of acetylcholine (procedure due to Buckett and Hackett, European J. Pharmacology, 1975, 30, 280). In general, compounds of formula I show significant activity in this test at an oral dose of 50 mg./kg. or less, without any overt toxic effects being seen, and preferred compounds of formula I show significant activity at an oral dose of 5 mg./kg., or less.

In addition to analgesic properties certain of the compounds of formula I possess anti-inflammatory properties which may be demonstrated using a standard test, for example, that involving adjuvant induced arthritis in rats and using a similar procedure to that of B. B. Newbould (British Journal of Pharmacology 1963, 21, 127).

A particular group of compounds of formula I which possess anti-inflammatory properties in addition to analgesic properties comprises the acids di-(4-chlorophenyl)methyleneamino-oxyacetic acid and 2-[di-(4-chlorophenyl)methyleneamino-oxy]propionic acid, the amides di-(4-chlorophenyl)methyleneamino-oxyacetamide and di-(4-chlorophenyl)methyleneamino-oxy-(N,N-diethyl)-acetamide, and the esters ethyl di-(4-chlorophenyl)-methyleneamino-oxyacetate and (2-dimethylamino)ethyl di-(4-chlorophenyl)methyleneamino-oxyacetate; and, where appropriate, pharmaceutically acceptable salts thereof.

In general compounds of formula I possessing anti-inflammatory properties show activity in the above test at an oral dose of 50 mg./kg. or less, given as a daily dose for 14 or 21 days, without overt toxic effects at the active dose.

When used to produce the aforementioned pharmacological effects in warm-blooded animals a compound of the invention may be administered as follows:

(a) for analgesic effects, at a daily oral dose of for example 5–25 mg./kg. of a compound of formula I; (in humans this is equivalent to a total daily dose of active ingredient of, for example, 125–625 mg.);

(b) for anti-inflammatory effects, at a daily oral dose of, for example, 5–50 mg./kg. of a compound of formula I possessing anti-inflammatory properties; (in humans this is equivalent to a total daily oral dose of active ingredient of, for example, 125–1250 mg.).

The above total daily doses may conveniently be given in divided, but not necessarily equal doses.

The compounds of the invention are conveniently administered in the form of pharmaceutical compositions which comprise a compound of formula I, or a pharmaceutically acceptable salt thereof as defined above, together with a pharmaceutically acceptable diluent or carrier. Such compositions are provided as a further feature of the invention, and may be in a form suitable for oral administration for example, in the form of a tablet, capsule, aqueous solution or suspension, oily solution or suspension, emulsion, dispersible powder, granule, syrup or elixir; or for parenteral administration, for example in the form of a sterile injectable aqueous or oily solution or suspension; or for rectal administration, as a suppository.

Such compositions may be prepared by conventional methods using conventional excipients. Convenient dosage unit forms of a composition of the invention contain for example, 50, 100, 200 or 500 mg. of an active ingredient of formula I or a salt thereof as defined above.

The compositions may be administered in the treatment of painful inflammatory joint diseases, for example, arthritis or osteoarthritis, and may also contain, in addition to an active ingredient of formula I, one or more agents possessing analgesic or anti-inflammatory properties, for example an agent selected from the following:

acetyl salicylic acid, paracetamol, dexpropoxyphene, codeine, chloroquine, phenylbutazone, D-pencillamine, indomethacin, ibuprofen, ketoprofen, naproxen, an anti-inflammatory steriod, for example prednisolone, and an organogold derivative, and a uricosuric agent, for example probenecid.

The invention is illustrated by the following non-limiting Examples wherein:

(i) all evaporations are carried out by rotary evaporation under reduced pressure;
(ii) petroleum ether (b.p. 60°–80° C.) is referred to as "petrol";
(iii) ambient temperature means at a temperature in the range 20°–25° C.;
(iv) yields (where given) are purely illustrative and are not to be construed as the maximum attainable for the process illustrated;
(v) solvents where indicated as dry are dried by conventional procedures.

EXAMPLE 1

Sodium hydride (0.45 g., 80% w/w suspension in mineral oil) was added gradually to a stirred solution of 4,4'-dichlorobenzophenone oxime (4.0 g.) in dry dimethylformamide (20 ml.) keeping the temperature below 30° C. After 30 minutes, ethyl bromoacetate (1.7 ml.) was added to the stirred solution and the temperature was allowed to rise to 30° C. After 16 hours stirring at ambient temperature the mixture was poured into water (100 ml.) and the subsequent mixture was extracted with ether. The combined extracts were washed with water, dried (MgSO$_4$) and evaporated to give ethyl di-(4-chlorophenyl)methyleneamino-oxyacetate, as an oil (3.8 g.), essentially pure and having a characteristic ester absorption at 1740–1760 cm$^{-1}$ in the infra-red spectrum.

EXAMPLE 2

A solution of ethyl di-(4-chlorophenyl)methyleneamino-oxyacetate (3.8 g.) in ethanol (140 ml.) and water (5 ml.) containing sodium hydroxide (5 g.) was heated under reflux for 16 hours. The mixture was then evaporated and the residue was diluted with water (100 ml.) and ether (50 ml.). The ether layer was separated and discarded. The aqueous layer was acidified to pH 2–3 by addition of 20% v/v hydrochloric acid and the solid (3.0 g.) which formed was separated and crystallised from ethyl acetate to give di-(4-chlorophenyl)-methyleneamino-oxyacetic acid, m.p. 147°–148° C., in 33% yield.

EXAMPLE 3

4,4'-Dichlorobenzophenone oxime (6.6 g.) was added to a solution of sodium (0.56 g.) in ethanol (50 ml.) and the mixture heated to 50° C. to obtain a clear solution. The solution was cooled to 20° C. and ethyl bromoacetate (4.2 g.) was added and the mixture stirred at room temperature for 16 hours. The mixture was evaporated and the residue extracted with ether and the ether evaporated. The residual oil was added to a column of dry chromatographic silica-gel [500 g., previously deactivated by addition of 10% w/w water and then equilibrated with 10% v/w of a mixture of toluene and petrol (5:1 v/v)]. The column was then eluted with the same mixture of toluene and petrol to give, after evaporation of solvent, ethyl di-(4-chlorophenyl)methyleneamino-oxyacetate, m.p. 49°–51° C., in 28% yield.

EXAMPLE 4

Sodium hydride (1.0 g., 80% w/w suspension in mineral oil) was added gradually to a stirred solution of di-(4-chlorophenyl)methyleneamino-oxyacetic acid (5.2 g.) in dry dimethylformamide (50 ml.) keeping the temperature below 30° C. After 30 minutes stirring N,N-dimethyl-2-chloroethylamine hydrochloride (2.3 g.) was added and the mixture stirred at 80° C. for 16 hours. The mixture was cooled, poured into water (100 ml.) and extracted with ether. The ether extract was shaken with acetic acid (2×50 ml. of 10% v/v aqueous solution) and the acid extract was separated and basified with sodium hydroxide (10% w/v). The mixture was extracted with ether, dried (MgSO$_4$) and evaporated. The residual oil was treated with excess ethereal hydrogen bromide to give 2-dimethylaminoethyl di-(4-chlorophenyl)methyleneamino-oxyacetate hydrobromide, m.p. 191°–192° C., (from ethanol), in 33% yield.

EXAMPLE 5

The procedure described in Example 1 was repeated except that ethyl bromoacetate was replaced by an equivalent amount of ethyl 2-bromopropionate or ethyl 2-bromo-2-methylpropionate. There were thus obtained ethyl 2-[di-(4-chlorophenyl)methyleneamino-oxy]propionate and ethyl 2-[di-(4-chlorophenyl)methyleneamino-oxy]-2-methylpropionate respectively in yields of 60–65%, obtained as oils, essentially pure and having characteristic absorption peaks in the infra-red spectrum at 1740–1760 cm$^{-1}$.

EXAMPLE 6

The procedure described in Example 1 was repeated except that 4,4'-dichlorobenzophenone oxime was replaced by an equivalent amount of 4,4'-dimethylbenzophenone oxime or 4,4'-difluorobenzophenone oxime. There were thus obtained ethyl di-(4-methylphenyl)methyleneamino-oxyacetate and ethyl di-(4-fluorophenyl)methyleneamino-oxyacetate respectively in yields of 55-65%, obtained as oils, essentially pure and having characteristic absorption peaks in the infra-red spectrum at 1740–1760 cm$^{-1}$.

EXAMPLE 7

The procedure described in Example 2 was repeated except that ethyl di-(4-chlorophenyl)methyleneamino-oxyacetate was replaced by the appropriate ester of formula VI wherein R$^4$ is an ethoxy radical. There were thus obtained the following acids of the formula:

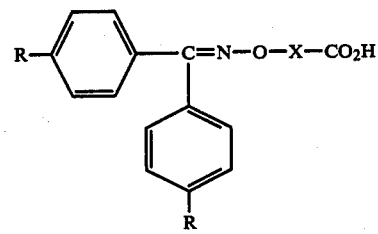

VII

| Compound No. | R | X | yield % | m.p. (°C.) | recrystallisation solvent(s) |
|---|---|---|---|---|---|
| 1 | chloro | CH$_3$<br>\|<br>—CH— | 49 | 124–125 | ethyl acetate/petrol |
| 2 | chloro | CH$_3$<br>\|<br>—C—<br>\|<br>CH$_3$ | 23 | 144–145 | ethyl acetate/petrol |
| 3 | methyl | —CH$_2$— | 21 | 152–153 | ethyl acetate |
| 4 | fluoro | —CH$_2$— | 25 | 116–118 | ethyl acetate |

EXAMPLE 8

Sodium hydride (0.7 g., 80% w/w suspension in mineral oil) was added gradually to a stirred solution of 4,4'-dichlorobenzophenone oxime (5.0 g.) in N-methyl-2-pyrrolidone (25 ml.) keeping the temperature below 30° C. After 10 minutes stirring butyrolactone (1.5 g.) was added and the mixture stirred at 150° C. for 3 hours. The mixture was evaporated and the residue poured into water (250 ml.). The mixture was filtered, and the filtrate acidified with glacial acetic acid. The mixture was extracted with ether, dried over magnesium sulphate and evaporated. The residual oil was dissolved in the minimum of ethyl acetate and mixed with one equivalent of benzylamine in petrol.

The mixture was filtered and the solid residue crystallised from ethyl acetate to give 4-[di-(4-chlorophenyl)methyleneamino-oxy]butyric acid benzylamine salt, m.p. 125°–126° C. in 38% yield.

EXAMPLE 9

Sodium hydride (0.5 g., 50% w/w suspension in mineral oil) was added gradually to a stirred solution of 4,4'-dichlorobenzophenone oxime (2.6 g.) in dry dimethylformamide (20 ml.) keeping the temperature below 30° C. After 30 minutes, chloroacetamide (0.9 g.) was added to the stirred solution keeping the temperature below 30° C. After 16 hours stirring at ambient temperature the mixture was poured into water (100 ml.) and the subsequent mixture extracted with ether. The combined extract was washed with water, dried (MgSO$_4$) and evaporated. The residue (2.5 g.) was added to a column of dry chromatographic silica-gel [300 g., previously deactivated by addition of 10% w/w water and then equilibrated with 10% v/w of a mixture of toluene and acetone (10:1 v/w)]. The column was then eluted with the same mixture of toluene and acetone to give, after evaporation of solvent, a solid residue (1.5 g.). The solid was recrystallised from ethyl acetate/petrol giving di-(4-chlorophenyl)methyleneamino-oxyacetamide m.p. 141°–142° C. (1.1 g.) in 34% overall yield.

EXAMPLE 10

The procedure described in Example 3 was repeated except that ethyl bromoacetate was replaced by an equivalent amount of N,N-diethyl chloroacetamide. There was thus obtained di-(4-chlorophenyl)methyleneamino-oxy-(N,N-diethyl)acetamide as a colourless oil, in 62% yield, and having the following characteristic NMR spectrum (in CDCl$_3$; chemical shifts in δ values):

1.12 (triplet, 6 protons, NCH$_2$C$\underline{H}_3$); 3.30 (multiplet, 4 protons, NC$\underline{H}_2$CH$_3$); 4.80 (singlet, 2 protons, OC$\underline{H}_2$); 7.31 (multiplet, 4 aromatic protons); 7.42 (singlet, 4 aromatic protons).

EXAMPLE 11

The procedure described in Example 3 was repeated, except that ethyl bromoacetate was replaced by an equivalent amount of ethyl 2-bromobutyrate. There was thus obtained ethyl 2-[di-(4-chlorophenyl)methyleneamino-oxy]butyrate as a colourless oil in 53% yield, essentially pure and having characteristic absorption peaks in the infra-red spectrum at 1740 cm$^{-1}$.

EXAMPLE 12

The procedure described in Example 2 was repeated except that ethyl di-(4-chlorophenyl)methylene aminooxyacetate was replaced by an equivalent amount of ethyl 2-[di-(4-chlorophenyl)methyleneamino-oxy]butyrate, and the heating with sodium hydroxide solution was limited to 4 hours. The reaction mixture obtained was then evaporated and the residue diluted with water (100 ml.). The mixture was acidified with concentrated hydrochloric acid and extracted with ether. The ether extracts were washed with dilute ammonia, and the alkaline washings were acidified with hydrochloric acid. The aqueous mixture was then extracted with ether, dried (MgSO$_4$) and evaporated. The residual oil was stirred with petroleum-ether (b.p. 40°–60° C.) and filtered. The solid residue (1.8 g.) was recrystallised from ethyl acetate/petrol, and there was thus obtained 2-[di-(4-chlorophenyl)methyleneamino-oxy]butyric acid, m.p. 115°–116° C. in 41% overall yield.

EXAMPLE 13

The procedure described in Example 3 was repeated except that 4,4'-dichlorobenzophenone oxime was replaced by an equivalent amount of 4,4'-dimethoxybenzophenone oxime. There was thus obtained ethyl di-(4-methoxy-phenyl)methyleneamino-oxyacetate as an oil in 36% yield, essentially pure and having characteristic absorption peaks in the infra-red spectrum at 1740–1760 cm$^{-1}$.

EXAMPLE 14

A solution of ethyl di-(4-methoxyphenyl)methyleneamino-oxyacetate (1.0 g.) in ethanol (20 ml.) and water (5 ml.) containing potassium hydroxide (1.0 g.) was left at ambient temperature for 16 hours. The solution was evaporated and the residue partitioned between ether and water. The aqueous layer was separated and acidified with concentrated hydrochloric acid. The mixture was extracted with ether, the extract dried (MgSO$_4$) and evaporated to give di-(4-methoxyphenyl)methyleneamino-oxyacetic acid as a solid (0.5 g.), m.p. 105°–107° C. (55% yield).

EXAMPLE 15

The procedure described in Example 1 was repeated except that 4,4'-dichlorobenzophenone oxime was replaced by an equivalent amount of 4-chloro-2',4'-dichlorobenzophenone oxime. There was thus obtained an oil which was stirred with petroleum-ether (b.p. 40°–60° C.) and filtered. The filtrate was then evaporated to give ethyl (4-chlorophenyl)(2,4-dichlorophenyl)methyleneamino-oxyacetate as an oil in 56% yield, essentially pure and having a characteristic ester absorption at 1740–1760 cm$^{-1}$ in the infra-red spectrum.

The 4-chloro 2',4'-dichlorobenzophenone oxime used as starting material was made as follows:

A mixture of 4-chloro 2',4'-dichlorobenzophenone (8 g.), hydroxylamine hydrochloride (2.9 g.), powdered potassium hydroxide (7.7 g.), ethanol (10 ml.) and water (2 ml.) was heated under reflux for 15 minutes. The mixture was poured into water (300 ml.) containing concentrated hydrochloric acid (30 ml.), and the precipitated oil was left to crystallise. The mixture was then filtered, and the solid residue (7.0 g., 83% yield) of 4-chloro-2',4'-dichlorobenzophenone oxime (m.p. 98°–100° C.) was used in the above process without further purification. A sample recrystallised from petrol also had m.p. 98°–100° C.

EXAMPLE 16

The procedure described in Example 12 was repeated except that ethyl-[di-(4-chlorophenyl)methyleneamino-oxy]butyrate was replaced by ethyl (4-chlorophenyl)(2',4'-dichlorophenyl)methyleneamino-oxyacetate. There was thus obtained an oil which was purified by dry-column chromatography on silica-gel, using a 5% v/w mixture of toluene and acetic acid as eluant. There was thus obtained (4-chlorophenyl)(2,4-dichlorophenyl)methyleneamino-oxyacetic acid, m.p. 91°–93° C., in 22% overall yield.

EXAMPLE 17

A mixture of 4,4'-dihydroxybenzophenone (2.1 g.) and amino-oxyacetic acid hemihydrochloride (1.2 g.) in pyridine (20 ml.) was heated at 95°–100° C. for 16 hours. The solution was then evaporated, and the residue diluted with water. The mixture was acidified with hydrochloric acid and extracted with ether. The ether solution was then shaken with excess sodium hydrogen carbonate solution. The aqueous layer was then separated, acidified with hydrochloric acid and extracted with ether. The extracts were dried (MgSO$_4$), filtered and evaporated. The residual oil was dissolved in ethyl acetate and mixed with one equivalent of benzylamine in ethyl acetate. The mixture obtained was filtered and the solid residue recrystallised from ethanol. There was thus obtained the benzylamine salt of di-(4-hydroxyphenyl)methyleneamino-oxyacetic acid, m.p. 188°–190° C. in 31% overall yield.

EXAMPLE 18

A mixture of 50 parts by weight of di-(4-chlorophenyl)methyleneamino-oxyacetic acid, 27 parts by weight of lactose, and 20 parts by weight of maize starch was thoroughly stirred, and a paste formed from 2 parts by weight of maize starch and 40 parts by weight of water was added and thoroughly mixed. The resulting mass was passed through a 16-mesh screen, dried at 60° C. to constant weight and then passed through a 20 mesh screen. 1 Part by weight of magnesium stearate was added to the granules thus obtained and the mixture was compressed by conventional means, into tablets containing 50, 100, 200 and 500 mg. of active ingredient, suitable for oral administration for therapeutic purposes.

EXAMPLE 19

A mixture of 50 parts by weight of di-(4-chlorophenyl)methyleneamino-oxyacetic acid, 33 parts by weight of calcium phosphate, 10 parts by weight of microcrystalline cellulose and 4 parts by weight of calcium carboxymethylcellulose was thoroughly stirred and a paste formed from 2 parts by weight of polyvinylpyrrolidone and 40 parts by weight of water was added and thoroughly mixed. The resulting mass was passed through a 16-mesh screen, dried at 60° C. to constant weight and then passed through a 20 mesh screen. 1 Part by weight of magnesium stearate was added to the granules thus obtained and the mixture was compressed, by conventional means, into tablets containing 50, 100, 200 and 500 mg. of active ingredient, suitable for oral administration for therapeutic purposes.

EXAMPLE 20

The procedure described in Example 18 or 19 was repeated except that the active ingredient was replaced by a compound of formula I, for example as described in any one of Examples 1, 3–8. There were thus obtained tablets containing 50, 100, 200 and 500 mg. of active ingredient suitable for administration for therapeutic purposes.

EXAMPLE 21

The procedure described in Example 18 or 19 was repeated except that the active ingredient was replaced by a compound of formula I described in any one of Examples 9–17. There were thus obtained tablets containing 50, 100, 200 and 500 mg. of active ingredient suitable for administration for therapeutic purposes.

What I claim is:

1. A compound of the formula:

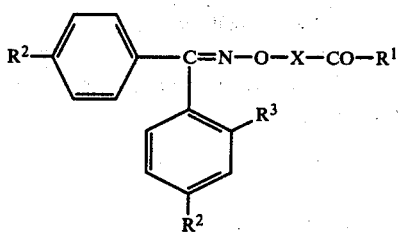

wherein $R^1$ is a hydroxy or $C_{1-4}$-alkoxy radical; $R^2$ is a halogen atom; $R^3$ is hydrogen or a halogen atom; and X is a methylene diradical; or, when $R^1$ is a hydroxy radical, a pharmaceutically acceptable base-addition salt thereof.

2. A compound according to claim 1 selected from the group consisting of di-(4-chlorophenyl)methyleneamino-oxyacetic acid and (4-chlorophenyl)(2,4-dichlorophenyl)methyleneamino-oxyacetic acid; and the pharmaceutically acceptable base-addition salts thereof; and ethyl di-(4-chlorophenyl)methyleneamino-oxyacetate.

3. A compound as claimed in claim 1 wherein $R^1$ is a hydroxy radical which is a sodium, potassium, calcium, magnesium, aluminium, triethanolamine or benzylamine salt.

4. A pharmaceutical composition which comprises a compound according to claim 1 or a pharmaceutically acceptable salt thereof in an amount sufficient to produce an analgesic effect, together with a pharmaceutically acceptable diluent or carrier.

5. A method for producing an analgesic effect in a warm blood animal requiring such treatment which comprises administering to said animal an effective amount of a compound according to claim 1 or a pharmaceutically acceptable salt thereof.

* * * * *